United States Patent [19]
Waddell et al.

[11] Patent Number: 4,727,862
[45] Date of Patent: Mar. 1, 1988

[54] FLOATING CENTER SPLINT OR HINGE

[76] Inventors: Thomas P. Waddell, 1306 Broadview West, Downingtown, Pa. 19335; Robin Renzetti, 2985 Hibernia Rd., Coatesville, Pa. 19320

[21] Appl. No.: 936,291

[22] Filed: Dec. 1, 1986

[51] Int. Cl.$^4$ .............................. A61F 5/04; A61F 5/01
[52] U.S. Cl. .................................. 128/80 C; 128/80 G
[58] Field of Search ................. 128/80 C, 80 R, 80 F, 128/80 G, 87 R, 88, 77

[56] References Cited

U.S. PATENT DOCUMENTS

| | | | |
|---|---|---|---|
| 2,980,110 | 4/1961 | Brumfield et al. | 128/87 R |
| 3,928,872 | 12/1975 | Johnson | 128/80 C |
| 4,130,115 | 12/1978 | Taylor | 128/80 C |
| 4,136,404 | 1/1979 | Lange | 128/80 R |
| 4,245,629 | 1/1981 | Cummins | 128/80 C |
| 4,450,832 | 5/1984 | Waddell | 128/80 C |
| 4,522,199 | 6/1985 | Waddell et al. | 128/80 G |
| 4,669,457 | 6/1987 | Hallisey | 128/80 C |

FOREIGN PATENT DOCUMENTS

| | | |
|---|---|---|
| 0039578 | 11/1981 | European Pat. Off. |
| 56069 | 6/1889 | Fed. Rep. of Germany |
| 58575 | 1/1890 | Fed. Rep. of Germany |
| 66490 | 4/1892 | Fed. Rep. of Germany |
| 838479 | 7/1949 | Fed. Rep. of Germany |
| 1478143 | 8/1970 | Fed. Rep. of Germany |
| 1578974 | 5/1972 | Fed. Rep. of Germany |
| 2238038 | 2/1973 | Fed. Rep. of Germany |

*Primary Examiner*—Edgar S. Burr
*Assistant Examiner*—Tonya Lamb

[57] ABSTRACT

A floating center variable radius splint or hinge for adjustably permitting angular motion of a body joint, to which the splint is connected, through a preselected angular range terminating at adjustably preselected minima and maxima and for preventing joint motion outside the range, includes a longitudinally extending spine adapted to flexibly bend, in response to joint motion, in a first transverse direction.

20 Claims, 22 Drawing Figures

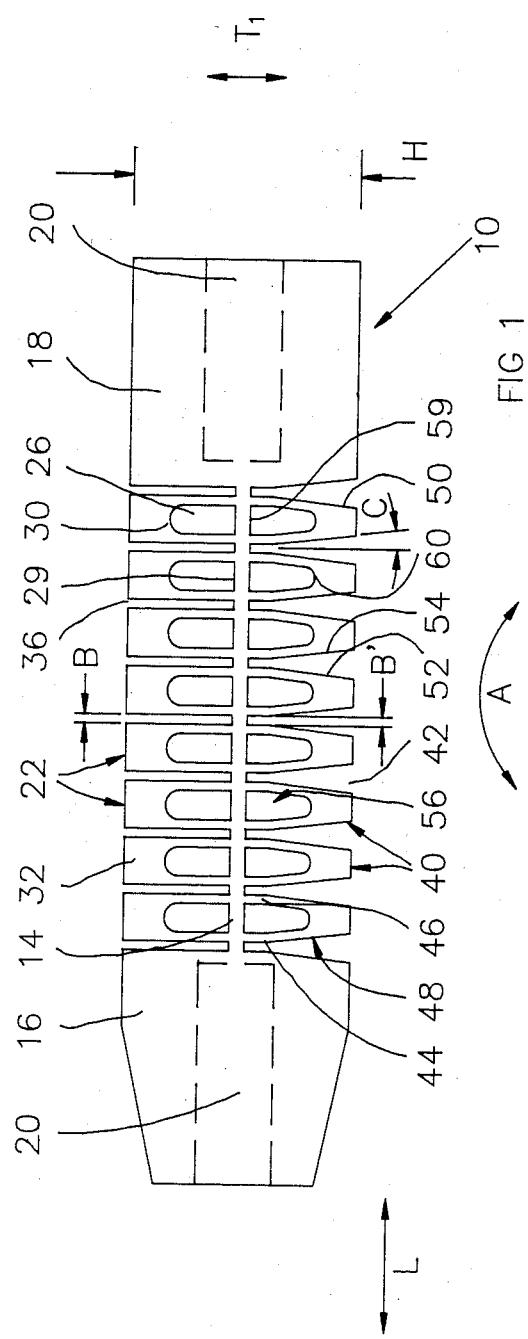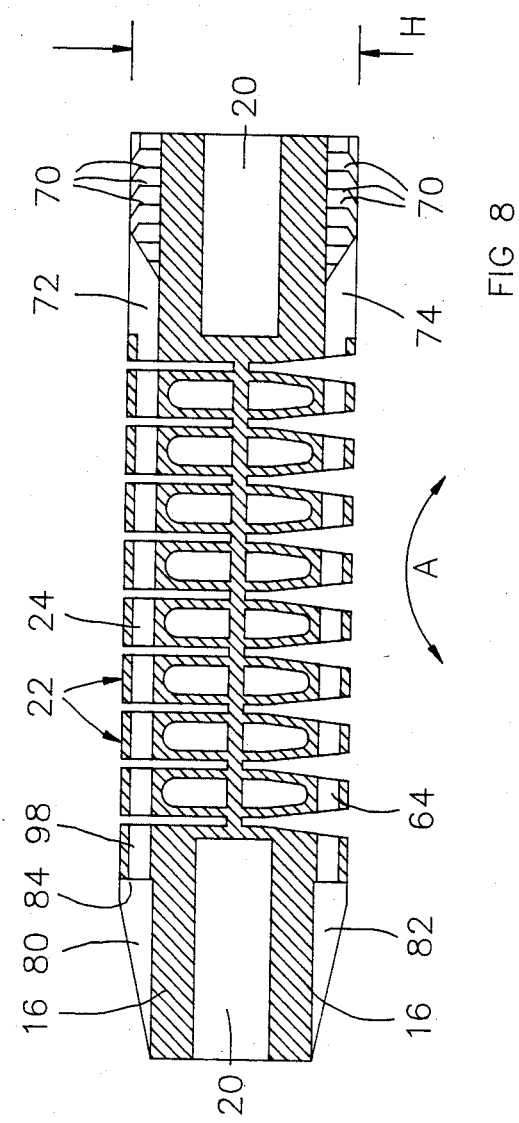

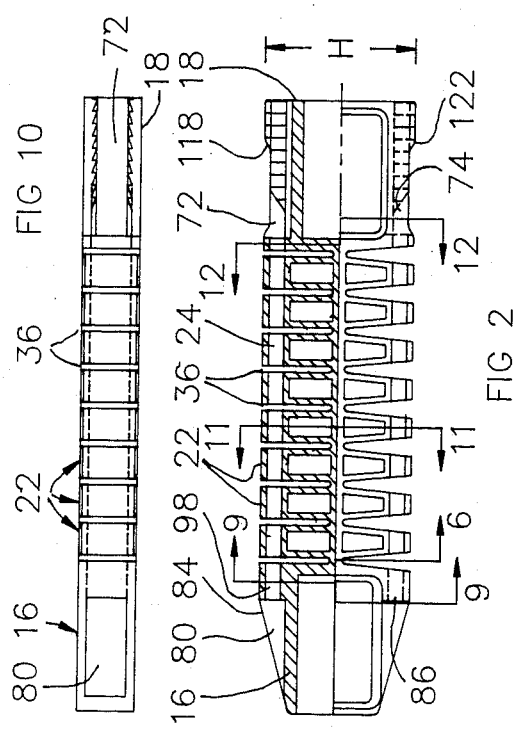

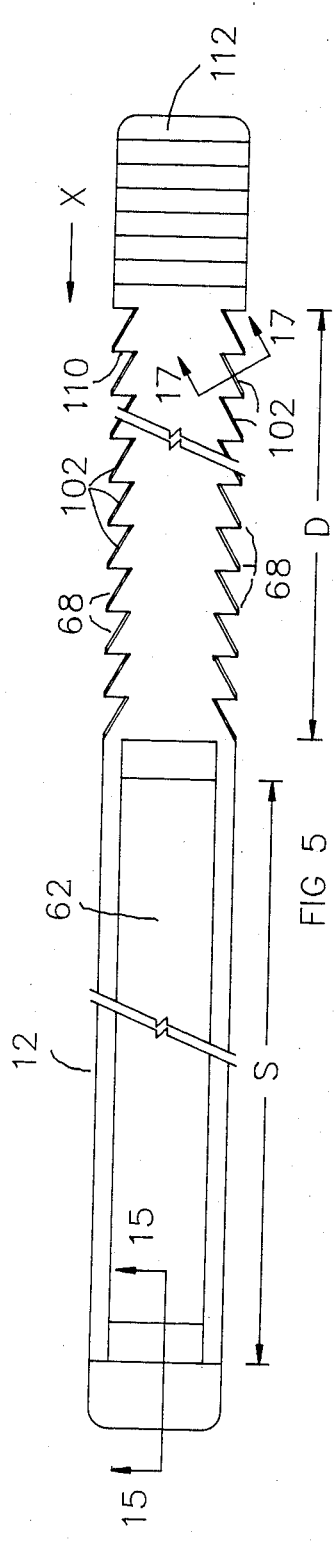
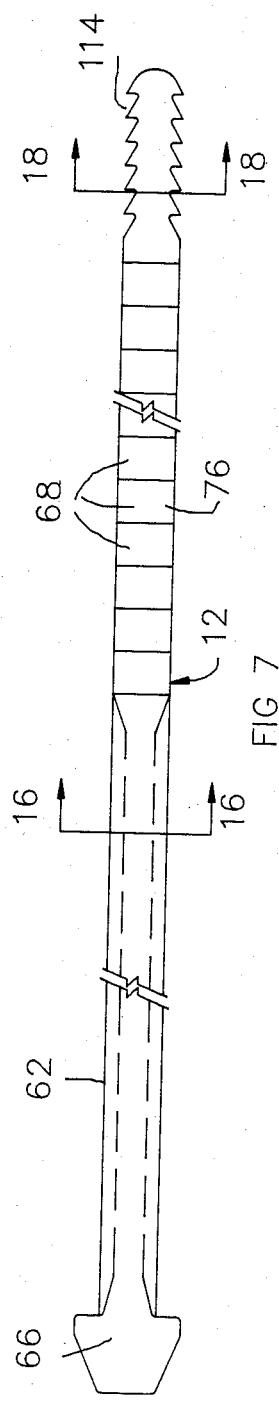
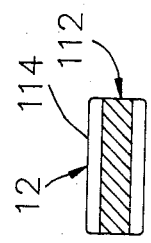
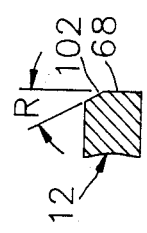
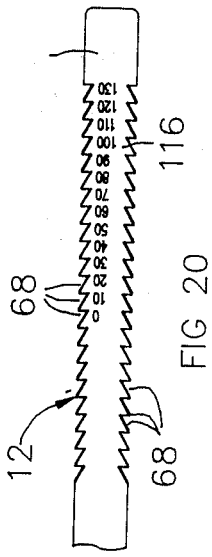
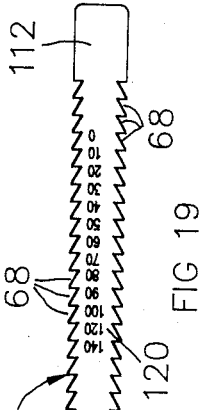

FLOATING CENTER SPLINT OR HINGE

BACKGROUND OF THE INVENTION

1. Field of the Invention

This invention relates to splints or hinges for use in postoperative, rehabilitative and injury prevention applications, to control or limit the range and direction of motion of a body joint or other body structure.

2. Description of the Prior Art

U.S. Pat. No. 4,450,832 discloses a body support system, including two support members, adapted for securement to the limbs of a user, with the support members connected by a flexible cable, carrying motion-affecting structure.

U.S. Pat. No. 4,522,199 discloses a body weight support system, including an upper support member above the knee and a lower support member below the knee having a lower end adjacent the foot, the support members being connected by a flexure assembly positionable behind the knee.

U.S. Pat. No. 3,928,872 discloses a leg support device for skiing, including an upper support means positionable above the knee and interconnected with a lower support means positionable below the knee by flexible spring means positionable alongside the knee.

U.S. Pat. No. 4,136,404 discloses an athletic leg brace, including a pair of lower leg brace members and a pair of upper leg brace members connected by ball joint hinges alongside the knee.

German Pat. No. 2,238,038 discloses a knee brace, including upper and lower half-tubes connected by a knee hinge and having a draw cord with one end connected to a ski binding on a ski, a middle portion slidably connected to the lower half-tube and the other end variably fixable to the upper half-tube.

German Pat. No. 838,479 discloses a joint for artificial limbs and support apparatus, including upper and lower support members connected together by overlying thin strips of spring steel sheet.

European Patent application No. 039,578 discloses a leg aid device, including bendable bias means extending from the ankle to mid-thigh and connected to upper and lower holders at each end and to two strap members about the knee.

German Pat. No. 58,575 discloses a device to facilitate walking, running and jumping, including a pair of rods extending alongside the legs and connected to a waist band on one end and shoes on the other, with the shoes being interconnected by straps which also connect to an elastic strip suspended from the waist band.

German Pat. No. 66,490 discloses apparatus to facilitate walking, including pairs of straps extending from a waist band to underneath the wearer's feet with each pair having three flexible strips to maintain the position of the straps.

German Pat. Nos. 56,069 and 1,393 disclose apparatus to facilitate walking, running and jumping, including pairs of flexible leg attachable support members fixed at each end about the waist and feet respectively, and flexible, resilient restraining members connected at one end to the foot and at the other end, at about waist high, a chain which extends down to the foot.

SUMMARY OF THE INVENTION

A floating center variable radius splint or hinge for adjustably permitting angular motion of a body joint, to which the splint is connected, through a preselected angular range terminating at adjustably preselectable minima and maxima and for preventing joint motion outside the range, includes a longitudinally extending spine adapted to flexibly bend, in response to joint motion, in a first transverse direction. The splint further preferably includes means, connected to the spine adjacent respective ends thereof for imparting adjustably predetermined initial minimum flex to the spine in the first transverse direction. This means preferably includes a first filament extending generally parallel with and displaced laterally from the spine and preferably includes means selectably engaging the first filament at a continuum of positions along first filament longitudinal length; these cooperate to adjustably vary effective length of the first filament connected to the spine. The splint further preferably includes means, connected to the spine adjacent respective ends thereof, for limiting spine flexure to an adjustably predetermined maximum of the angular range. This preferably includes a second filament extending generally parallel with and displaced laterally from the spine and means selectably engaging the second filament at a continuum of positions along second filament longitudinal length; these cooperate to adjustably vary effective length of second filament connected to the spine.

The means selectably engaging the filaments further preferably includes means for releasably locking portions of the filaments against longitudinal movement relative to the spine.

The means selectably engaging the filaments along continua of positions are preferably located proximate respective associated ends of the spine. The means for imparting initial flex to the spine and the means for limiting spine flexure preferably include means for slideably engaging the respective filaments proximate respective remaining ends of the spine. The continua of positions on the filaments are preferably closer to first ends of the filaments than to remaining ends of the filaments. The remaining ends of the filaments preferably include means for resisting passage of the remaining ends of the filaments along the means slideably engaging the filaments.

The splint may further preferably include a first member cantilevered from the spine in the first transverse direction, slideably engaging the first filament intermediate respective first filament ends. The splint may still further preferably include an adjacent plurality of first members cantilevered from the spine in the first transverse direction, slideably engaging the first filament intermediate the respective first filament ends, with the first members being longitudinally spaced one from another when the spine is at the preselected minimum of the angular range.

The splint may still further preferably include a second member cantilevered from the spine in the first transverse direction, oppositely from the first member, slideably engaging the second filament intermediate respective second filament ends. The splint may still further preferably include an adjacent plurality of second members cantilevered from the spine in the first transverse direction, oppositely from the first members, slideably engaging the second filament intermediate respective second filament ends. The spine longitudinal cross-section preferably has minimum dimension in the first transverse direction. The filament longitudinal cross-sections preferably have minimum dimensions in the first transverse direction.

The means for imparting adjustably predetermined initial minimum flex to the spine in the first transverse direction further preferably include terminal block members connected to the spine adjacent respective ends thereof.

The means selectably engaging the filaments at continua of positions along filament longitudinal lengths, for adjustably varying effective filament length connected to the spine and for releasably locking portions of the filaments against longitudinal movement relative to the spine, further preferably include channels in the terminal block members for receiving respective filaments and receptacles in the channels for complementarily releasably receiving corresponding projecting portions of respective filaments.

The means for slideably engaging the respective filaments proximate respective remaining ends of the spine further preferably include passageways, in respective terminal block members at opposite ends of the spine from the channels, adapted for free sliding passage of central portions of the filaments therethrough.

The filaments further preferably include projecting portions of suitable size for complemental receipt by the receptacles, extending longitudinally along the filaments proximate first filament ends to define the continua of positions. The filaments also preferably include enlarged portions at filament ends remote the projecting portions, for precluding passage of ends of the filaments through the terminal block members.

The spine preferably has generally rectangular longitudinal cross-section. The first and second cantilevered members preferably have generally rectangular transverse cross-sections. The filaments preferably have generally rectangular longitudinal cross-sections. The mutually facing surfaces of adjacent ones of the first cantilevered members diverge one from another at positions remote from juncture with the spine.

The mutually facing surfaces of the first cantilevered members each preferably include two planar portions, first ones of the planar portions adjoining and generally perpendicular to the spine and parallel one to another when the spine is unflexed, with second ones of the planar portions defining the diverging mutually facing surfaces.

The first cantilevered members may preferably include orifices for passage therethrough of the first filament. The orifices in the first cantilevered members define a passageway parallel to the spine. The mutually facing surfaces of adjacent ones of the second cantilevered members are preferably parallel one with another when the spine is unflexed. The mutually facing surfaces of the second cantilevered members are preferably planar. The second cantilevered members preferably include orifices for passage therethrough of the second filament. The orifices in the second cantilevered members define a passageway parallel to the spine. The projecting portions preferably have generally saw-tooth configuration and project transversely from the filaments.

The passageways through the first and second pluralities of cantilevered members are preferably proximate respective transverse extremities of the cantilevered members, remote the spine. The first and second pluralities of the cantilevered members are preferably respectively longitudinally aligned. The transversely outwardly facing surfaces of the first and the second pluralities of cantilevered members are preferably planar.

Th planar transversely outwardly facing surfaces of the first plurality of cantilevered members are preferably coplanar when the spine is unflexed. The planar transversely outwardly facing surfaces of the second plurality of cantilevered members are preferably coplanar when the spine is unflexed.

The saw-tooth configured projecting members preferably have transversely extending surfaces facing the ends of the filaments remote from the end to which the saw-tooth configured projecting members are proximate.

The saw-tooth configured projecting members preferably have outwardly facing surfaces, angularly disposed with respect to longitudinal axes of the filaments. The angularly disposed surfaces connect outer extremities of the transversely extending surfaces with inner extremities of immediately adjacent saw-tooth configured projecting members.

The angularly disposed outwardly facing surfaces of the projecting members are preferably beveled. The channels preferably have beveled outwardly facing edges in the area of the receptacles.

The receptacles are preferably saw-tooth configured and preferably include transversely extending surfaces facing the ends of the respective terminal block members housing the receptacles remote from respective terminal block connection with the spine. The saw-tooth configured receptacles preferably have outwardly facing surfaces, which are angularly disposed with respect to longitudinal axes of the channels, connecting transverse outer extremities of the transversely extending surfaces of the receptacles with transverse inner extremities of immediately adjacent saw-tooth configured receptacles. The receptacles are preferably transversely recessed within the channels relative to the beveled outwardly facing edges of the channels.

The receptacles preferably include generally planar bottom surfaces perpendicular to the longitudinal direction and to the transverse direction.

The receptacles are preferably undercut at juncture of the angularly disposed outwardly facing surfaces with the beveled outwardly facing edges of the channels. The undercuts may be complemental with the beveled outwardly facing angled surfaces of the filaments when the filaments are lockingly engaged with the selectable engaging means.

The cantilevered members preferably have transverse passageways therethrough, inboard of the longitudinally aligned orifices thorough which the filaments pass, proximate juncture of the cantilevered members with the spine.

The spine and the cantilevered members are preferably integrally formed of homogeneous material. The spine, the cantilevered members and the terminal blocks are preferably thermoplastic, for example polypropylene, and are preferably injection molded as a unitary assembly in a single step injection molding operation.

In another of its aspects the invention provides a floating center variable radius splint or hinge for permitting angular motion of a body joint to which the splint is connected through a preselected angular range terminating at a preselectable maximum and preventing joint motion outside the range. This embodiment includes a longitudinally extending spine adapted to flexibly bend, in response to joint motion, in a first transverse direction and means, connected to the spine adjacent respective ends thereof, for limiting spine flexure to an adjustably predetermined maximum of the angular range. This embodiment preferably includes a plurality of first members cantilevered from the spine in the first transverse direction, spaced apart one from another when the spine is unflexed and abuttingly contacting adjacent ones with another upon spine flexure in the first transverse direction to a preselected angle corresponding to the preselected angular range maximum. This embodiment further preferably includes a plurality of second members cantilevered from the spine in the first transverse direction but facing oppositely from the first cantilevered members, spaced apart one from another when the spine is unflexed and abuttingly contacting adjacent ones with another upon spine flexure in the direction of projection of the second cantilevered members, oppositely to the direction in which the spine is adapted to flex. This embodiment further may preferably include means, connected to the spine adjacent respective ends thereof, for imparting adjustably predetermined initial minimum flex to the spine in the first transverse direction, which means may preferably include a filament extending generally parallel with and displaced laterally from the spine along with means selectably engaging the filament at a continuum of positions along filament longitudinal length, for adjustably varying effective filament length connected to the spine.

The first cantilevered members may slideably engage the filament intermediate respective filament ends. The first and second cantilevered members preferably have generally rectangular transverse cross-sections. The filament preferably has generally rectangular longitudinal cross-section. The mutually facing surfaces of adjacent ones of the first cantilevered members diverge one from another at positions remote from juncture with the spine.

The mutually facing surfaces of the first cantilevered members may each preferably include two planar portions, with first ones of the planar portions adjoining and generally perpendicular to the spine and parallel one to another when the spine is unflexed and with second ones of the planar portions defining the diverging mutually facing surfaces.

The first cantilevered members may preferably include orifices for passage therethrough of the filament. The orifices in the first cantilevered members may define a passageway parallel to the spine. The mutually facing surfaces of adjacent ones of the second cantilevered members are preferably parallel one with another when the spine is unflexed. The mutually facing surfaces of the second cantilevered members are preferably planar.

The passageways through the first plurality of cantilevered members are preferably proximate respective transverse extremities of the cantilevered members, remote from the spine. The first and the second pluralities of the cantilevered members are preferably respectively longitudinally aligned. The transversely outwardly facing surfaces of the first and the second pluralities of cantilevered members are preferably planar. The planar transversely outwardly facing surfaces of the first plurality of cantilevered members are preferably coplanar when the spine is unflexed and the planar transversely outwardly facing surfaces of the second plurality of cantilevered members are preferably coplanar when the spine is unflexed.

In yet another of its aspects the invention is manifested as a floating center variable radius splint or hinge for either permitting angular motion of a body joint to which the splint is connected to commence at an adjustably preselectable minimum angle or preventing angular motion of the body joint from continuing past an adjustably preselectable maximum angle. The splint or hinge preferably includes a longitudinally extending spine adapted to flexibly bend, in response to joint motion, in a first transverse direction. Means are preferably connected to the spine adjacent respective ends thereof, for either imparting adjustably predetermined initial flex to the spine, thereby permitting angular motion of the body joint to commence at an adjustably preselectable minimum angle, or limiting spine flexure to an adjustably predetermined maximum, thereby preventing angular motion of the body joint from continuing past an adjustably preselectable maximum angle. These means preferably include a filament extending generally parallel with and displaced laterally from the spine, means selectably engaging the filament at a continuum of positions along filament longitudinal length for adjustably varying effective filament length connected to the spine and means for releasably locking a portion of the filament against longitudinal movement relative to the spine.

The means selectably engaging the filament along a continuum of positions is preferably located proximate an end of the spine. The means for either imparting initial flex to the spine or limiting spine flexure further preferably include means for slideably engaging the filament proximate the remaining end of the spine.

This embodiment of the invention further preferably includes means for limiting spine flexure to an absolute maximum at least equal to the adjustably predetermined maximum and preferably includes a plurality of members cantilevered from the spine in the first transverse direction, spaced apart one from another when the spine is preferably unflexed and abuttingly contacting adjacent ones with another upon spine flexure in the first transverse direction to the absolute maximum.

The cantilevered members preferably have generally rectangular transverse cross-sections. The filament preferably has generally rectangular longitudinal cross-section. The mutually facing surfaces of adjacent ones of the cantilevered members diverge one from another at positions remote from juncture with the spine.

The mutually facing surfaces of the cantilevered members each preferably include two planar portions, first ones of the planar portions adjoining and generally perpendicular to the spine and parallel one to another when the spine is unflexed and second ones of the planar portions defining the diverging mutually facing surfaces.

The cantilevered members preferably include orifices for passage therethrough of the filament. The orifices in the cantilevered members define a passageway parallel to the spine. The passageways through the first plurality of cantilevered members are preferably proximate respective transverse extremities of the cantilevered members, remote the spine. The cantilevered members are preferably longitudinally aligned. The transversely outwardly facing surfaces of the cantilevered members are preferably planar. The planar transversely outwardly facing surfaces of the cantilevered members are preferably coplanar when the spine is unflexed.

BRIEF DESCRIPTION OF THE DRAWINGS

FIG. 1 is a front elevation of a schematic representation of a portion of a splint embodying aspects of the invention.

FIG. 2 is a front elevation, partially longitudinally sectioned, of a portion of a splint embodying aspects of the invention; the structure illustrated in FIG. 2 corresponds to the structure illustrated schematically in FIG. 1. FIG. 2 is sectioned as indicated by lines and arrows 2—2 in FIG. 3.

FIG. 3 is a side elevation, viewed from the right hand side, of structure illustrated in FIG. 2.

FIG. 4 is a side elevation, viewed from the left hand side, of structure illustrated in FIG. 2.

FIG. 5 is a top view of another portion of a splint embodying aspects of the invention, which structure illustrated in FIG. 5 engages structure illustrated in FIG. 2.

FIG. 6 is a bottom view of structure illustrated in FIG. 2.

FIG. 7 is a side view of structure illustrated in FIG. 5.

FIG. 8 is a longitudinal central sectional view of structure represented schematically in FIG. 1.

FIG. 9 is a sectional view of structure illustrated in FIGS. 2, 3, 4 and 6, taken at lines and arrows 9—9 in FIG. 2.

FIG. 10 is a top view of structure illustrated in FIG. 2.

FIG. 11 is a sectional view taken at lines and arrows 11—11 in FIG. 2.

FIG. 12 is a sectional view taken at lines and arrows 12—12 in FIG. 2.

FIG. 13 is an enlarged broken view of a portion of the structure of FIG. 6 enclosed by circle 13.

FIG. 14 is an enlarged broken sectional view taken at lines and arrows 14—14 in FIG. 13.

FIG. 15 is a broken sectional view taken at lines and arrows 15—15 in FIG. 5.

FIG. 16 is a sectional view taken at lines and arrows 16—16 in FIG. 7.

FIG. 17 is a broken sectional view taken at lines and arrows 17—17 in FIG. 5.

FIG. 18 is a sectional view taken at lines and arrows 18—18 in FIG. 7.

FIGS. 19 and 20 are broken schematic views of respective alternate embodiments of the right hand portion of the structure illustrated in FIG. 5.

FIG. 22 is an enlarged broken view of the structure of FIG. 13 engaged with a portion of the structure of FIG. 5.

Figure 21:
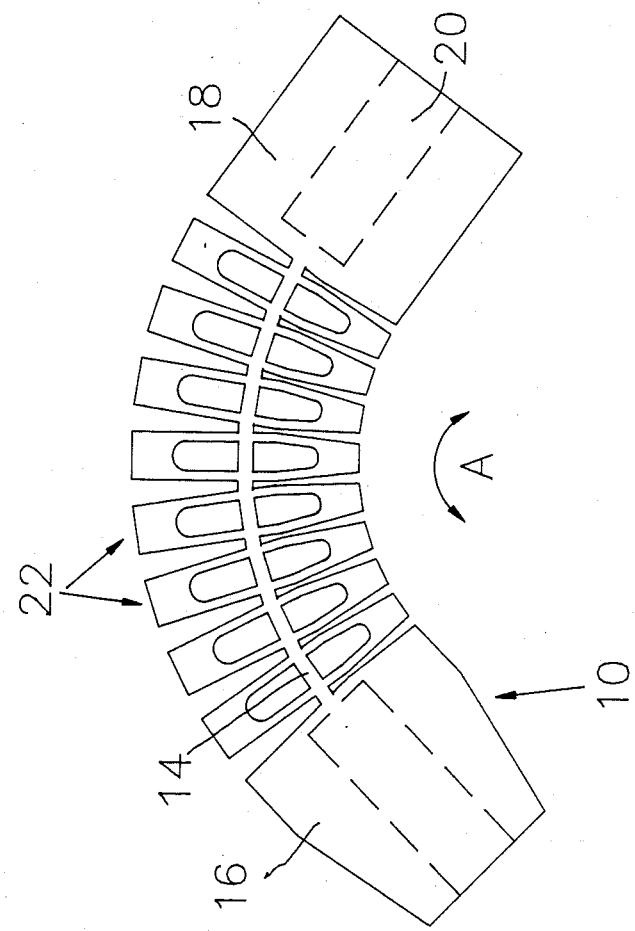
FIG. 21 is a front elevation of a schematic representation of a portion of a flexed splint embodying aspects of the invention.

DESCRIPTION OF THE PREFERRED EMBODIMENTS AND BEST MODE KNOWN FOR PRACTICING THE INVENTION

Apparatus embodying a portion of the floating center variable radius splint manifesting aspects of the invention is illustrated schematically in FIGS. 1 and 21 and in greater detail in FIG. 2 and is designated generally 10. Portion 10, referred to hereinafter as a first portion of the adjustable floating center variable radius splint is preferably a single piece of injection molded plastic, longitudinally elongated as illustrated generally in FIGS. 1, 2, 6, 8, 10 and 21.

A second portion of the floating center variable radius splint is designated generally 12 and is illustrated in FIGS. 5 and 7. It is to be understood that in the preferred embodiment the splint of the invention includes not only first portion 10 but also two, generally similar second portions 12, differing slightly from one another as described below, with each of the second portions 12 engaging first portion 10, in a manner described in greater detail below. In other embodiments, the splint of the invention includes only first portion 10 as illustrated in FIGS. 1, 2, 6, 8 and 10 while in still other embodiments the splint of the invention includes first portion 10 as illustrated in FIGS. 1, 2, 6, 8, 10 and 21 and a single second portion 12 as illustrated generally in FIGS. 5 and 7.

Further referring to FIGS. 1, 2, 6, 8, 10 and 21 in general and to FIGS. 1 and 2 specifically, first portion 10 includes a central longitudinally extending spine 14 which is preferably of generally rectangular band-like configuration and is adapted to bend flexibly in response to motion of a human or animal joint to which the floating center variable radius splint of the invention has been closely affixed. Spine 4 is configured, due to its cross-section shape and size to flex most easily generally in the direction indicated by arrow A in FIGS. 1 and 21. Arrow A illustrates the preferred manner of bending or flexure of spine 14 along a first direction, indicated by arrow T1 in FIG. 1, transverse to the direction of longitudinal elongation of spine 14. Flexure of spine 14 in the manner indicated by arrow A is preferred. The direction indicated by arrow T1 is generally referred to as a first transverse direction. Arrow L in FIG. 1 denotes the longitudinal direction.

Connected to either end of spine 14 and formed integrally and unitarily therewith are respective terminal blocks 16, 18, illustrated in FIGS. 1, 2, 6, 8, 10 and 21. Terminal block 16 is referred to as a first terminal block while terminal block 18 is referred to as a second terminal block. Terminal blocks 16 and 18 may have hollow centers designated generally 20 and shown in dotted lines in FIGS. 1 and 21 but in solid lines in FIGS. 2, 3, 4, 6, 8 and 10. These hollow centers 20 are provided so that the floating center, variable radius splint of the invention may easily be secured to suitable means for connecting attachment to limbs or other body parts of a human or animal, which limbs or other body parts extend away from a joint or other body part of interest whose motion is being restrained using the floating center variable radius splint of the invention. The respective means for connecting attachment, which fit into recesses 20 and secure the floating center variable radius splint of the invention to the patient, form no part of the invention.

As best seen in FIGS. 1, 2, 8, 10, 11 and 21, a plurality of first members, individual ones of which are preferably of block-like rectangular configuration and are designated 22 in FIGS. 1 and 2, extend in cantilever fashion away from spine 14 along the first transverse direction indicated by arrow T1 in FIG. 1 and opposite to the direction of preferred curved flexure of spine 14 as denoted by arrows A. Cantilevered members 22 are preferably of generally rectangular cross-section in the longitudinal direction and in both directions transverse to spine 14. First cantilevered members 22 preferably have generally rectangular cross-sectional, longitudinal passageways 24 therethrough, as illustrated in FIGS. 10 and 11. Passageways 24 are suitably sized and shaped for free sliding engagement of the central part of a second or filament portion 12 of the floating center variable radius splint assembly embodying the invention, which is generally illustrated in FIGS. 5 and 7.

In addition to longitudinal passageways 24 in first cantilevered members 22, these members 22 may have open centers defined by transverse passageways 26 through first cantilevered members 22, in a second transverse direction, perpendicular to both the longitudinal direction L and the first transverse direction T1, as illustrated in FIGS. 1, 2, 8 and 11. Transverse passageways 26 have generally rectangular bottoms, with passageway bottom surfaces being defined by spine 14, and may have generally arch-shaped tops as illustrated in FIG. 1; the bottoms and tops of passageways 26 are denoted 28, 30 respectively in FIGS. 1 and 2.

Rectangular portions 32 of respective first cantilevered members 22, which portions 32 are relatively remote from central spine 14, are connected to spine 14 via two leg members 34 of first cantilevered members 22. Leg members 34 have solid cross-section in the longitudinal direction indicated by arrow L in FIG. 1. First cantilevered members 22 are positioned along spine 14 in spaced apart relationship one to another, where the spaces are indicated generally 36 in FIG. 1; adjacent members 22 are separated one from another by distance B shown in FIG. 1, when spine 14 is unflexed.

Longitudinal passageways 24 and 64 through first block-like cantilevered members 22 are illustrated in FIG. 8 and are longitudinally and transversely aligned one with another to permit free sliding passage of a central part of a second portion 12 of the injection molded spline of the invention therethrough, through and relative to all of first cantilevered members 22.

First portion 10 further includes a plurality of second cantilevered members extending generally oppositely from spine 14 relative to first cantilevered members 22, in the first transverse direction. Individual second cantilevered members of the plurality are designated generally 40 in FIG. 1. Second cantilevered members 40 are spaced one from another at their respective bases where they integrally join spine 14 by space preferably corresponding to space 36; spaces separating members 40 are designated 42 in FIG. 1. Dimension B in FIG. 1 indicates the length of space 36 in the longitudinal direction while dimension B' indicates the length of space 42 adjacent to spine 14. Dimensions B and B' are preferably the same for both first and second cantilevered members 22, 40; however, this is not required.

Second cantilevered members 40 are preferably configured identically to first cantilevered members 22 where those members join spine 14. As illustrated in FIGS. 1, 2, 8 and 11, second cantilevered members 40 extend perpendicularly away from spine 14 and have leg portions 44 corresponding generally to leg portions 34 of first cantilevered members 22. As is apparent from FIGS. 2 and 11 leg portions 44 have generally rectangular cross section in the first transverse direction. Second cantilevered members taper in the first transverse direction as illustrated in FIGS. 1, 2 and 8. Specifically, second cantilevered members extend generally outwardly from spine 14 with leg portions 44 having first segments 46 which are generally perpendicular with respect to spine 14. Tapered portions 48 of second cantilevered members 40 extend outwardly from portions 46 of legs 44, which are generally transverse to spine 14, with tapered portion 48 terminating to form an outwardly facing surface generally parallel with the longitudinal axis of spine 14. This outwardly facing surface is designated 50 in FIG. 1.

Tapered portions 48 are tapered, with respect to a first transverse axis through spine 14, at an angle C as illustrated in FIG. 1. Angle C is selected to define maximum permissible angular flexure of spine 14 in the direction indicated by arrow A in FIG. 1. Specifically, when first portion 10 is flexed to a maximum permissible angle in the direction indicated by arrow A, mutually facing tapered surfaces 52, 54 of adjacent second cantilevered members 40 abuttingly contact one another thereby precluding further angular flexure of first portion 10 in the direction of arrow A. The greater the taper of angle C, the greater the flexure of first portion 10 before mutually facing surfaces 52, 54 abut one another and preclude further motion.

Second cantilevered members 40 have transverse passageways 56 extending therethrough in the second transverse direction where passageways 56 are similar to transverse passageways 26 through first cantilevered members 22. Passageways 56 have generally flat bottoms 58 defined by a longitudinally extending surface of spine 14 and have tops 60, which may be arched with the arch generally facing bottom surface 58, all as illustrated in FIG. 1. Arched construction of the top of passageway 56, with legs 44 of second cantilevered members 40 forming the sides of the arch, provides high strength for second cantilevered member 40 extending transversely outwardly from spine 14.

As illustrated in FIG. 1, second cantilevered members 40 are separated one from another by distance B' which may preferably be about the thickness of leg portions 44 of second cantilevered members 40 in the longitudinal direction. As further illustrated in FIG. 1, longitudinal length of flat bottoms 58 of passageways 56 may be two or more times the thickness in the longitudinal direction of leg portions 44. These same characteristics apply with respect to first cantilevered members 22, dimension B, space 36 and leg portions 34.

The preferred rectangular configuration of first cantilevered members 22 and their relatively close spacing as illustrated in FIGS. 1 and 2 precludes any substantial amount of flexure of spine 14 in the direction opposite to that indicated by curved arrow A in FIG. 1. This is because upon any significant flexure of spine 14 in the direction opposite to curved arrow A, mutually facing surfaces of adjacent block-like members 22, defining space 36 therebetween, abuttingly contact each other, preventing further flexure of spine 14.

First and second cantilevered members 22, 40 are preferably similar one to another, differing substantially only in the taper provided on second cantilevered members 40 by tapered portions 48 and mutually facing surfaces 52, 54 manifesting such taper. The degree to which flexure of spine 14, in direction opposite curved arrow A, is precluded may be controlled by selecting space 36 and dimension B to be greater or lesser, as required. The smaller dimension B, the less flexure of spine 14 in the direction opposite that of curved arrow A will be possible.

Second portion 12 of the variable radius floating center splint is illustrated in FIGS. 5, 7 and 15 through 20 and includes a central portion designated generally 62 of preferably rectangular or I-beam longitudinal cross-section, suitably sized for free fitting, sliding engagement in longitudinal passageways 24 or 64 of first or second cantilevered members 22, 40. The preferred cross-sectional configuration of central portion 62 is illustrated in FIG. 16. Second or filament portion 12 further includes an enlarged tabular end portion 66 having longitudinal cross-section in excess of the longitudinally projected area of passageway portions 98, 100 of channels 80, 82 formed in terminal block 16, as described in more detail below; this cross-section is of sufficiently large size to preclude passage of second or filament portion 12 through longitudinal passageways 24, 64. At the end of second filament portion 12 opposite that of tabular end portion 66 is formed a series of tooth-like projections 68 in the lateral side of second filament portion 12 proximate the end thereof as illustrated in FIGS. 5 and 7. Tooth-like projections 68 are formed along a length of second or filament portion 12 indicated as dimension D in FIG. 5. A corresponding complemental series of grooves 70 are formed in respective channels 72, 74 which are in turn formed in second terminal block 18 and are aligned with longitudinal passageways 24, 64 respectively. Channels 72, 74 have width dimensioned for free sliding engagement of central portion 62 of filament portion 12 along the channel. Tooth-like projections 68 are formed on a tongue-like extension of second or filament portion 12 with tongue-like extension 76 defining an end portion of filament portion 12 opposite to tabular end portion 66. Tongue-like portion 76 has essentially the same longitudinal cross-sectional periphery as that of the central portion 62 of filament portion 12.

The splint of the invention in the preferred embodiment is assembled by inserting two second or filament portions 12 into longitudinal extending passageways within first portion 10, where those passageways are defined respectively by channels 80, 82 in first terminal block 16, longitudinally aligned passageways 24, 64 formed respectively in first and second block-like cantilevered members 22, 40 and channels 72, 74 in second terminal block 18. The second or filament portions are inserted first into channels 80 or 82 with tongue-like portions 76 being inserted first. The second or filament portion is then urged through passageways 24 or 64, through first or second block-like cantilevered members 22, 40 respectively and finally into channels 72 or 74. Second or filament portion 12 is fed through this series of passageways with one such filament portion being fed through each series of passageways so that the fully assembled splint includes two filament portions positioned generally parallel with spine 14 and transversely displaced therefrom. The two filament portions are inserted into the channels until tabular end portions 66 abut shoulders 84, 86 formed in terminal block 16. Second or filament portions 12 may then be adjusted, to flex spine 14 to a desired degree of initial flexure and to control flexure of spine 14 to a predetermined, desired maximum by adjustable postioning of second or filament portions 12, by fitting tooth-like projections 68 into grooves 70 formed in respective channels 72, 74, as set forth below.

Each groove 70, as illustrated in greater detail in FIG. 13, is formed as an undercut in a wall 83 laterally bounding channel 74. Each groove 70 as formed has a transverse edge 90 and an angled edge 92 connecting with transverse edge 90 at a vertex 94 transversely displaced from channel 74. A generally saw-tooth configuration of grooves 70 results from the serial repetition of the transverse edge-angled edge pattern, as best illustrated in FIG. 13. Vertex 94 at which transverse and angled edges of a single groove meet is referred to as an outboard vertex while vertex 96 at which a transverse edge of a first groove 70 meets an angled edge of a second or adjacent groove is referred to as an inboard vertex. The groove 70 and associated transverse and angled edges 90, 92 and vertices 94, 96 are formed in both lateral sides of channel 74. Similar grooves 70 are formed in channel 72, as illustrated in FIGS. 6, 10 and 13.

Each groove 70 is slightly undercut into the wall of the channel in which the groove is formed; as illustrated in FIG. 14, the undercut is formed in wall 88 of channel 74 and results in groove 70 being slightly wider at the intermediate portion of the groove than at the top of the groove. This undercut is indicated as 104 in FIG. 14.

The configuration of tooth-like projections 68 and grooves 70 in second and first portions 12, 10 respectively of the splint of the invention provide means for selectably lockingly engaging second portion 12 in first portion 10 to prevent relative longitudinal motion therebetween. Each second portion 12 includes a series of tooth-like projections 68 extending therefrom as generally illustrated in FIGS. 5, 7, 19 and 20. Each tooth-like projection 68 is beveled, as indicated at 102 in FIG. 17 with the angle of bevel indicated as angle R in FIG. 17. Another, somewhat corresponding undercut 104 is formed at the top of groove 70 as best illustrated in FIG. 14. Undercut 104 connects a lateral side surface 106 of groove 70 with a tapered upwardly facing surface 108 defining the opening of channel 74 in first portion 10. Undercut 104 is bevelled so that lateral wall 106, in the area of the groove 70, is transversely outboard of the vertex formed at juncture of bevelled undercut 104 and bevelled surface 108 formed on the outer surface of groove 170. This same configuration as is illustrated generally in FIGS. 13 and 14 is applied to the grooves 70 formed both in channels 72 and 74 in second terminal block 18 of first portion 10. Similarly, bevel 102 on tooth 68 illustrated in FIG. 17 may be provided at all teeth 68 formed on the transversely outwardly facing lateral surfaces of second portion 12. The angle between transverse edge 90 of groove 70 and angled edge 92 of groove 70 is essentially the same for all grooves 70 and corresponds to the similar angle formed at the outer extremity of tooth-like projections 68. FIG. 22 shows in detail engagement of projections 68 and grooves 70.

Each tooth-like projection 68 has a transversely extending surface 110 facing longitudinally towards the end of second portion 12 at which teeth 68 are formed. Transversely extending surface 110 complementally engages transverse edge 90 of groove 70 when second portion 12 is locked in position against relative longitudinal motion with respect to first portion 10. The mutually facing orientation of surface 110 and surface 90 precludes movement of second portion of 12 longitudinally with respect to first portion 10, in the direction indicated generally by arrow X in FIG. 5, in the area of tooth-groove mating.

The beveled configuration of surface 108 in combination with the undercut provided by surface 104 in channel 70 provides a snap-action by which a user of the splint of the invention can easily snap second portion 12 into place with teeth 68 engaging complemental groove 70 thereby preventing relative motion of an end of second portion 12 with respect to first portion 10 in the direction indicated by arrow X. Similarly, the configurations of these surfaces make it relatively easy for the user to pop second portion 12 out of locking engagement with first portion 10, when it is desired to adjust the splint.

Further provided at the end of second portion 12 remote from enlarged tabular end portion 68 is a tongue member 112 having grooves 114 formed therein in the second transverse direction. Tongue 112 and grooves 114 provide a handle or tab for easy gripping of second portion 12 by a user or physician adjusting the splint.

In a preferred embodiment of the invention, two second portions 12 are utilized, one of greater length then the other. The two portions differ in length principally in the area indicated by dimension S in FIG. 5; otherwise the portions are preferably, but not necessarily, essentially structurally identical. When two filaments or second portions 12 are utilized, the portions of greater length is installed with central portion 62 in sliding, free engagement with passageways 24 in first cantilevered members 22 and with respective ends of second portion 12, as represented principally by tabular end portion 66 and tooth-like projections 68 respectively, engaging channel 80 in first terminal block 16 and channel 72 in second terminal block 18. This second portion 12 serves to limit flexure of spine 14 to an adjustably preselected maximum. Teeth corresponding to teeth 68 are engaged with grooves corresponding to 70 formed in channel 72.

The second portion 12, which resides in passageways 24 and channels 72, 80 all as illustrated at the upper portion of FIG. 8, effectively limits flexure of spine 14 to a preselected maximum by contacting shoulder 84, formed in first terminal block 16 and defining an end of passageway portion 98, with tabular end portion 66 of second portion 12.

When the splint is first placed in use, the second portion engaging passageways 24 and associated channels at the upper portion of FIG. 8 will have its teeth 68 engaging grooves 70 formed in channel 72 and will have tabular end portion 66 remote from shoulder 84 and separated therefrom by a length of central portion 62. The longitudinal length of second portion 12 on which teeth 68 are formed substantially exceeds the longitudinal length of channel 72 in which grooves 70 are formed. Thus second portion 12 can be positioned at any of a continuum of positions with respect to second terminal block 18 and can be locked in position against longitudinal movement with respect thereto. The appropriate position of the second portion 12 engaging passageways 24 and associated grooves at the upper portion of FIG. 8 is indicated by suitable indicia 116 which are printed, embossed or otherwise made to appear on the surface of second portion 12 laterally bounded by teeth 68, as illustrated in FIG. 20. These indicia are keyed to the amount of angular flex permitted of spine 14 for a given position of second portion 12 with respect to first portion 10. Typically indicia 116 may be positioned relative to a scribe line or other indicator such as provided by the rise 118 at the top of second terminal block 18 as illustrated in FIG. 2.

In the preferred embodiment of the invention a second portion 12 is positioned in engagement with passageway 64 and associated channels 82, 74 illustrated at the lower portion of FIG. 8 and is used to provide a predetermined initial amount of flex to spine 14. This second second portion 12 also includes indicia indicated as 120 in FIG. 19, which indicate the amount of predetermined flex applied to spine 14 for any given position of second second portion 12 with respect to first portion 10. Similarly to indicia 116, indicia 120 may be keyed to rise 122 formed in second terminal block 18 as illustrated in FIG. 2.

In operation, if a predetermined initial flex is to be applied to spine 14, the second second portion 12 is slidably inserted into passageways 64, from left to right as illustrated in FIG. 8, until tabular end portion 66 abuts shoulder 86, illustrated in FIG. 2, defining a terminus of passageway portion 100 of channel 82 formed in first terminal block 16. Tongue 112 of second portion 12 is then pulled to the right in the drawings, thereby causing spine 14 to flex in the direction indicated by curved arrow A in FIGS. 1 and 8. When spine 14 has flexed to the predetermined desired initial degree of flexure, teeth 68 of second second portion 12 are engaged with grooves 70 in channel 74; alternatively, tongue 112 can be pulled to the right in the drawings until the desired initial flex of spine 14 has been achieved as indicated by a selected indicia 120 being aligned with rise 122. At this point, thumb pressure is applied to second portion 12 in the neighborhood of teeth 68 with the pressure applied in the first transverse direction, forcing teeth 68 to snap into engagement with grooves 70 in passageway 74. Because tabular end portion 66 of second portion 12 abuts shoulder 86, spine 14 will be retained with this initial degree of flex and is not permitted to relax back to the zero flex state until the second portion in passageway 64 and associated channels 74, 82 is disengaged from grooves 70 by moving tongue 112 downwardly in FIG. 8 thereby snapping teeth 68 out of engagement with grooves 70.

Operation of second portion 12 which engages passageways 24 and associated channels 72, 80 is converse of operation of second portion 12 which engages passageway 64, in that second portion 12 engaging passageways 24 does not have its tabular end portion 66 abutting shoulder 84 until spine 14 flexes to the predetermined maximum amount. When spine 14 has flexed to this amount, tabular portion 66 of second portion 12 engaging passageways 24 contacts shoulder 84 thereby preventing further flexure of spine 14. Due to spine 14 having flexed an amount in addition to the predetermined initial flex, the tabular end portion 66 of second portion 12 engaging passageways 64 will have moved away from shoulder 86 when the spine is at the maximum flexed condition. As spine 14 moves within the permissible angular range, neither of tabular end portions 66 contact shoulders 84 or 86, unless the spine reaches one of the end points of its range of permissible angular travel. FIG. 21 shows the invention in a flexed condition.

Second cantilevered members 40 are configured with angle C so that these members, by abutting contact one with another, prevent flexure of spine 14 in excess of a predetermined absolute maximum. Similarly, abutting contact of first cantilevered members 22 one with another prevents any significant amount of flex of spine 14 in the direction opposite that shown by curved arrow A.

The invention may be further utilized with only one of second portions 12 engaging first portion 10, as generally described above. In such a case, the invention can be used to provide a splint or hinge which will either prevent angular motion of the associated joint from exceeding a preselected maximum or will assure that the joint is always bent at least to an amount corresponding to the predetermined initial minimum flex of spine 14.

The invention may further be utilized with neither of the two second portions 12, and instead relying upon second cantilevered numbers 40 to limit flex of spine 14 to a predetermined absolute maximum and relying on first cantilevered members 22 to prevent flex of spine 14 in any substantial amount in the direction opposite that indicated by curved arrow A.

The cross-section of spine 14 and filaments or second portions 12 in the longitudinal direction are selected to provide substantial resistance to flexure in any direction other than that of the first transverse direction indicated by arrow T1 and curved arrow A in FIG. 1. Similarly, the generally rectangular configuration of the cantilevered members and their generally rectangular cross-sections in the first and second transverse directions, as well as in the longitudinal direction, provides additional stability to the splint or hinge and further assists in preventing flexure of the splint or hinge in any direction other than the first transverse direction. With the rectangular configuration of first cantilevered members 22 essentially preventing flexure of spine 14 in the first transverse direction other than as indicated by curved arrow A in FIG. 1, the configuration of the splint or hinge provides a high degree of stability and resistance to bending in any direction other than as indicated by curved arrow A.

While it is preferred that the splint or hinge of the invention be fabricated with first portion 10 made in a single injection molding operation, it is to be understood that first portion 10, as well as second portions or filaments 12, can be fabricated of composite materials to impart even greater strength to the hinge of the invention. Particularly, it is envisioned that longitudinally extending, generally rectangularly crossed-sectioned bands of high strength material, such as fiberglass or carbon fiber, may be utilized as part or all of spine 14 and as part or all of second or filament portions 12.

The configuration of first portion 10 permitting flexure of spine 14, in response to movement of a body joint or other part to which the spline is connected, does not restrict spine 14 to rotating or flexing about any fixed center. Indeed, the center of rotation of the splint can be located anywhere; it does not need to be aligned or symmetrical with spine 14. Consequently, should the splint or the associated connecting structure slip relative to the joint having its motion constrained, the splint may still function and not place an unnatural, potentially devastating load on the joint being treated.

As yet another advantage of the invention, because the flexure characteristics of rectangular cross-section members such as spine 14 are relatively well known and can be calculated with a high degree of accuracy for any given material, the invention has ergonomic applications in that the splint of the invention may be fabricated, by selection of appropriate materials and be design choice of appropriate cross-section shapes and sizes, to provide a predetermined, regulated degree of resistance to flexure of spine 14 where the resistance is inherent from the construction of spine 14 of selected material and of suitable shape and size. Thus the invention may eliminate the need for externally applied load(s) to provide predetermined, relatively constant resistance to flexure to a body joint to which the splint or hinge of the invention is connected.

When the invention is constructed with portion 10 fabricated of injection molded thermoplastic, the preferred thermoplastic is polypropylene.

While the longitudinal cross-sections of spine 14 and second portions 12 have been illustrated as being generally rectangular, other cross-sectional configurations may be used to provide different bending characteristics and the like as desired. However, the rectangular cross-section is preferable, to provide the greatest resistance against flexure of spine 14 in any direction other than is indicated by curved arrow A.

In one preferred embodiment the invention has been fabricated with first portion 10 having an overall length of about 6 inches, with first and second cantilevered members 22, 40 occupying total length of about 3 inches and with first and second terminal blocks 16, 18 each being about 1 and ½ inches in length. First portion 10 has been about ½ inch wide in the second transverse direction and has been about 1 and ½ inches wide in the first transverse direction; this corresponds to a height H in FIGS. 1, 2 and 8. Second portion 12 has been fabricated in two lengths. The second portion engaging passageways 24 has been about 6½ inches long while the second portion engaging passageways 64 has been about 5½ inches long. The angle at the vertex of teeth 68 has been about thirty degrees and the bevel indicated by angle R in FIG. 17 has been about forty degrees. The central portion 62 of second portion 12 has been about four-tenths of an inch wide in the second transverse direction and has had width, of the rectangular cross-section portion of the I beam, of about one quarter of an inch. The corners of second portion 12 have been rounded with a radius of about thirty-six thousandths of an inch; this rounding provides greater assurance of free sliding passage of second portion 12 through the various grooves and passageways through which free sliding passage is required. Teeth 68 occupy a length of second portion 12 of about 2.3 inches while the tooth portions of grooves 72, 74 have been only about one inch in length. The bevel of surface 108 has been about ten degrees while the angle of undercut 104 has been about forty degrees, both of these being measured with respect to the vertical in FIG. 14. Dimension B in FIG. 1 has been about sixty-two thousandths of an inch as has dimension B' prime. Angle C has been from 15 to 25 degrees.

In this regard it should be noted that it is not necessary for the second cantilevered members 40 to be symmetrically tapered. These members can be tapered more on sides facing generally towards first terminal block 16 than on sides facing second terminal block 18, or visa versa. Spine 14 has been about on eighth of an inch thick in the first transverse direction.

While the foregoing dimensions are not intended to limit the generality of the invention, they do provide indication of the relative sizes of the parts of the invention which have been found to provide a splint, which when constructed of polypropylene, provides excellent stability against flexure of spine 14, and any associated joint, in any direction other than as indicated by curved arrow A, provides excellent stability to the associated joint and generally has been found to be highly satisfactory in operation. However, it is to be understood that the invention is not limited to any of these dimensional characteristics or attributes and that the invention can be practiced in any of the configurations noted above with none, one or two second portions 12 in appropriate engagement with first portion 10.

As in yet another advantage provided by the geometric configuration illustrated in the drawings, the splint or hinge has generally planar outwardly facing surfaces in the unflexed condition and even in the flexed condition, when fully flexed, externally facing surfaces 50 of second cantilevered members 40 present an essentially continuous surface. These surface characteristics reduce the chances for the splint or hinge catching fabric, bandages or the like carried by the user, thereby reducing the chances for interference with operation of the splint or hinge by such fabric or bandages and reducing the chances for the splint or hinge to tear the garments or bandages worn by the user.

We claim:

1. A floating center, variable radius splint, for adjustably permitting angular motion of a body joint to which said splint is connected through a preselected angular range terminating at adjustably preselectable minima and maxima and preventing joint motion outside said range, comprising:
   a. a longitudinally extending spine adapted to flexibly bend, in response to joint motion, in a first transverse direction;
   b. means, connected to said spine adjacent respective ends therof, for imparting adjustably predetermined initial minimum flex to said spine in said first transverse direction, including:
      1. a first filament extending generally parallel with and displaced laterally from said spine;
      2. means selectably engaging said first filament at a continuum of positions along first filament longitudinal length, for adjustably varying effective length of first filament connected to said spine;
   c. means, connected to said spine adjacent respective ends thereof, for limiting spine flexure to an adjustably predetermined maximum of said angular range, including:
      1. a second filament extending generally parallel with and displaced laterally from said spine;
      2. means selectably engaging said second filament at a continuum of positions along second filament longitudinal length, for adjustably varying effective length of second filament connected to said spine.

2. Apparatus of claim 1 wherein said means for selectably engaging said filaments further comprises means for releasably locking said filaments against longitudinal movement relative to said spine.

3. Apparatus of claim 2 wherein said means selectably engaging said filaments along continua of positions are located proximate one end of said spine and wherein said means for imparting initial flex to said spine and said means for limitng spine flexure include means for slideably engaging said filaments proximate the remaining end of said spine.

4. Apparatus of claim 3 wherein said continua of positions on said filaments are closer to first ends of said filaments than to remaining ends of said filaments and wherein said remaining ends of said filaments include means for resisting passage of said remaining ends of said filaments along said means slideably engaging said filaments.

5. Apparatus of claim 4 further comprising a first member cantilevered from said spine in said first transverse direction, slideably engaging said first filament intermediate respective first filament ends.

6. Apparatus of claim 5 further comprising an adjacent plurality of said first members cantilevered from said spine in said first transverse direction, slideably engaging said first filament intermediate said respective first filament ends, said first members being longitudinally spaced one from another when said spine is at the preselected angular range minimum.

7. Apparatus of claim 5 further comprising a second member cantilevered from said spine in said first transverse direction, oppositely from said first cantilevered member, slideably engaging said second filament intermediate respective second filament ends.

8. Apparatus of claim 7 further comprising an adjacent plurality of second members cantilevered from said spine in said first transverse direction, oppositely from said plurality of first cantilevered members, slideably engaging said second filament intermediate said respective second filament ends.

9. Apparatus of claim 7 wherein said spine longitudinal cross-section has minimum dimension in said first transverse direction.

10. Apparatus of claim 9 wherein said filament longitudinal cross-sections have minimum dimensions in said first transverse direction.

11. Apparatus of claim 10 wherein said means for imparting adjustably predetermined initial minimum flex to said spine in said first transverse direction further comprises:
   a. terminal block members connected to said spine adjacent respective ends thereof;
wherein said means selectably engaging said filaments at continua of positions along filament longitudinal lengths for adjustably varying effective filament length connected to said spine and releasably locking said filaments against longitudinal movement relative to said spine further comprises:
   b. channels in said terminal block members for receiving respective filaments therein;
   c. receptacles in said channels for complementarily releasably receiving corresponding projecting portions of respective filaments;
wherein said means for slideably engaging said respective filaments proximate respective remaining ends of said spine further comprise:
   d. passageways in respective terminal block members at opposite ends of said spine from said channels, adapted for free sliding passage of central portions of said filaments therethrough;
wherein said filaments further comprise:
   e. projecting portions of suitable size for complemental receipt by said receptacles, extending longitudinally along said filaments proximate first filament ends to define said continua of positions;
   f. enlarged portions at filament ends remote said projecting portions, having longitudinal cross sections in excess of longitudinal projected area of said terminal block member passageways, for precluding passage of said ends of said filaments through said terminal block members.

12. Apparatus of claim 11 wherein said spine has generally rectangular longitudinal cross-section;
   wherein said first and second cantilevered members have generally rectangular transverse cross-sections;
   wherein mutually facing surfaces of adjacent ones of said first cantileved members diverge one from another at positions remote from juncture with said spine;
   wherein said mutually facing surfaces of said first cantilevered members each include two planar portions, first ones of said planar portions adjoining and generally perpendicular to said spine and parallel one to another when said spine is unflexed and second ones of said planar portions defining said diverging mutually facing surfaces;
   wherein said first cantilevered members include orifices for passage therethrough of said first filament;
   wherein said orifices in said first cantilevered members define a passageway parallel to said spine;

wherein mutually facing surfaces of adjacent ones of said second cantilevered members are parallel one with another when said spine is unflexed;

wherein said mutually facing surfaces of said second cantilevered members are planar;

wherein said second cantilevered members include orifices for passage therethrough of said second filament;

wherein said orifices in said second cantilevered members define a passageway parallel to said spine;

wherein said projecting members have generally sawtooth configuration and project transversely from said filaments;

wherein said passageways through said first and second pluralities of cantilevered members are proximate respective transverse extremities of said cantilevered members, remote said spine;

wherein said first and said second pluralities of said cantilevered members are respectively longitudinally aligned;

wherein transversely outwardly facing surfaces of said first and said second pluralities of cantilevered members are planar;

wherein said planar transversely outwardly facing surfaces of said first plurality of cantilevered members are coplanar when said spine is unflexed and said planar transversely outwardly facing surfaces of said second plurality of cantilevered members are coplanar when said spine is unflexed;

wherein said saw-tooth configured projecting members have transversely extending surfaces facing said ends of said filaments remote from the end to which said saw-tooth configured projecting members are proximate;

wherein said saw-tooth configured projecting members have outwardly facing surfaces, angularly disposed with respect to longitudinal axes of said filaments, connecting outer extremities of said transversely extending surfaces with transverse inner extremities of transversely extending surfaces of immediately adjacent saw-tooth configured projecting members;

wherein said angularly disposed outwardly facing surfaces of said projecting members are beveled;

wherein said channels have beveled outwardly facing edges in the area of said receptacles;

wherein said receptacles are saw-tooth configured and include transversely extending surfaces facing said ends of said respective terminal block members housing said receptacles remote from position of respective terminal block connection with said spine;

wherein said saw-tooth configured receptacles have outwardly facing surfaces, angularly disposed with respect to longitudinal axes of said channels, connecting transverse outer extremities of said transversely extending surfaces of said receptacles with transverse inner extremities of said transversely extending surfaces of immediately adjacent sawtooth configured receptacles;

wherein said receptacles are transversely recessed within said channels relative to said beveled outwardly facing edges of said channels;

wherein said receptacles include generally planar bottom surfaces perpendicular to said longitudinal direction and to said transverse direction;

wherein said receptacles are undercut at juncture of said receptacle angularly disposed outwardly facing surfaces with said beveled outwardly facing edges of said channels, said undercuts facing said beveled outwardly facing angled surfaces of said filaments when said filaments are lockingly engaged with said selectable engaging means.

13. Apparatus of claim 12 wherein said cantilevered members have transverse passageways therethrough, inboard of said longitudinally aligned orifices thorough which said filaments pass, proximate juncture of said cantilevered members with said spine.

14. Apparatus of claim 12 wherein said spine and said cantilevered members are integrally formed of homogeneous material;

wherein said spine and said cantilevered members are thermoplastic;

wherein said thermoplastic is polypropylene.

15. A floating center, variable radius splint, for permitting angular motion of a body joint to which said splint is connected through a preselected angular range terminating at a preselectable maximum and preventing joint motion outside said range, comprising:

a. a longitudinally extending spine adapted to flexibly bend, in response to joint motion, in a first transverse direction;

b. means, connected to said spine adjacent respective ends thereof, for limiting spine flexure to an adjustably predetermined maximum of said angular range, including:

1. a plurality of first members cantilevered from said spine in said first transverse direction, spaced apart one from another when said spine is unflexed and abuttingly contacting adjacent ones with another upon spine flexure in said first transverse direction to a preselected angle corresponding to the preselected angular range maximum;

2. a plurality of second members cantilevered from said spine in said first transverse direction oppositely from said first cantilevered members, spaced apart one from another when said spine is unflexed and abuttingly contacting adjacent ones with another upon spine flexure in the direction of projection of said second cantilevered members, oppositely to the direction in which said spine is adapted to flex.

16. Apparatus of claim 15 further comprising means, connected to said spine adjacent respective ends thereof, for imparting adjustably predetermined initial minimum flex to said spine in said first transverse direction, including:

1. a filament extending generally parallel with and displaced laterally from said spine;

2. means selectably engaging said filament at a continuum of positions along filament longitudinal length, for adjustably varying effective filament length connected to said spine;

wherein one of said pluralities of cantilevered members slideably engage said filament intermediate respective filament ends.

17. Apparatus of claim 16 wherein said first and second cantilevered members have generally rectangular transverse cross-sections;

wherein mutually facing surfaces of adjacent ones of said first cantilevered members diverge one from another at positions remote from juncture with said spine;

wherein said mutually facing surfaces of said first cantilevered members each include two planar portions, first ones of said planar portions adjoining and generally perpendicular to said spine and parallel one to another when said spine is unflexed and second ones of said planar portions defining said diverging mutually facing surfaces;

wherein mutually facing surfaces of adjacent ones of said second cantilevered members are parallel one with another when said spine is unflexed;

wherein said mutually facing surfaces of said second cantilevered members are planar.

18. A floating center, variable radius splint, for either permitting angular motion of a body joint to which said splint is connected to commence at an adjustably preselectable minimum angle or preventing angular motion of said body joint to which said splint is connected from continuing past an adjustably preselectable maximum angle, comprising:

a. a longitudinally extending spine adapted to flexibly bend, in response to joint motion, in a first transverse direction;

b. means, connected to said spine adjacent respective ends thereof, for either imparting adjustably predetermined initial flex to said spine thereby permitting angular motion of a body joint to which said splint is connected to commence at an adjustably preselectable minimum angle or limiting spine flexure to an adjustably predetermined maximum thereby preventing angular motion of said body joint to which said splint is connected from continuing past an adjustably preselectable maximum angle, including:

1. a filament extending generally parallel with and displaced laterally from said spine;

2. means selectably engaging said filament at a continuum of positions along filament longitudinal length, for adjustably varying effective filament length connected to said spine and including means for releasably locking said filament against longitudinal movement relative to said spine;

wherein said means selectably engaging said filament along a continuum of positions is located proximate an end of said spine;

wherein said means for either imparting initial flex to said spine or limiting spine flexure further comprises means for slideably engaging said filament proximate said remaining end of said spine.

19. Apparatus of claim 18 further comprising means for limiting spine flexure to an absolute maximum at least equal to said adjustably predetermined maximum, including a plurality of members cantilevered from said spine in said first transverse direction, spaced apart one from another when said spine is unflexed and abuttingly contacting adjacent ones with another upon spine flexure in said first transverse direction to the absolute maximum.

20. Apparatus of claim 19 wherein said cantilevered members have generally rectangular transverse cross-sections;

wherein mutually facing surfaces of adjacent ones of said cantilevered members diverge one from another at positions remote from juncture with said spine;

wherein said mutually facing surfaces of said cantilevered members each include two planar portions, first ones of said planar portions adjoining and generally perpendicular to said spine and parallel one to another when said spine is unflexed and second ones of said planar portions defining said diverging mutually facing surfaces;

wherein said cantilevered members include orifices for passage therethrough of said filament;

wherein said orifices in said cantilevered members define a passageway parallel to said spine;

wherein said passageways through said cantilevered members are proximate respective transverse extremities of said cantilevered members, remote said spine;

wherein said cantilevered members are longitudinally aligned.

* * * * *